(12) United States Patent
Danielsson et al.

(10) Patent No.: US 6,429,578 B1
(45) Date of Patent: Aug. 6, 2002

(54) DIAGNOSTIC AND THERAPEUTIC DETECTOR SYSTEM FOR IMAGING WITH LOW AND HIGH ENERGY X-RAY AND ELECTRONS

(76) Inventors: Mats Danielsson, Stockholmsvägen 45 A, S-182 78, Stocksund; Anders Brahme, Långbackavägen 22, S-182 33, Danderyd, both of (SE)

( * ) Notice: Subject to any disclaimer, the term of this patent is extended or adjusted under 35 U.S.C. 154(b) by 0 days.

(21) Appl. No.: 09/236,596

(22) Filed: Jan. 26, 1999

(51) Int. Cl.⁷ .................................. H01J 43/00
(52) U.S. Cl. ............... 313/105 CM; 313/103 CM; 313/105 CM; 250/374; 250/385.1
(58) Field of Search ............... 313/542, 544, 313/103 R, 103 CM, 105 R, 365, 523, 532, 533, 538; 250/211 VT, 214 VT, 374, 385.1

(56) References Cited

U.S. PATENT DOCUMENTS

| | | | |
|---|---|---|---|
| 5,044,002 A | | 8/1991 | Stein |
| 5,192,861 A | * | 3/1993 | Breskin et al. ............. 313/534 |
| 5,233,990 A | | 8/1993 | Barnea |
| 5,521,956 A | | 5/1996 | Charpak ..................... 378/146 |
| 5,604,783 A | | 2/1997 | Charpak ..................... 378/146 |
| 5,656,887 A | * | 8/1997 | Voshell et al. ....... 313/105 CM |
| 5,688,698 A | | 11/1997 | Robinson et al. |
| 6,011,265 A | * | 1/2000 | Sauli ......................... 250/374 |

OTHER PUBLICATIONS

"Development of the Gas Electron Multiplier", Benlloch et al., IEEE Nuclear Science Symposium and Medical Imaging Conference, Albuquerque, New Mexico, Nov. 9–15, 1997, pp 1–10.

* cited by examiner

Primary Examiner—Michael H. Day
Assistant Examiner—Joseph Williams
(74) Attorney, Agent, or Firm—Young & Thompson

(57) ABSTRACT

A detector unit for detecting photons in the energy range 1 keV to 100 MeV, includes at least two converter layers adapted to interact with incident X-ray photons and to cause electrons to be emitted therefrom, at least one amplifier adapted to interact with the electrons emitted from the converters and adapted to produce a multiplicity of secondary electrons and photons representing a signal proportional to the incident fluence of X-ray photons, a connector connecting the detector to an electric field generator providing an electric drift field for secondary electrons in the detector, and a sensor device arranged to receive the signal and provide an input to electronic signal processor.

23 Claims, 9 Drawing Sheets

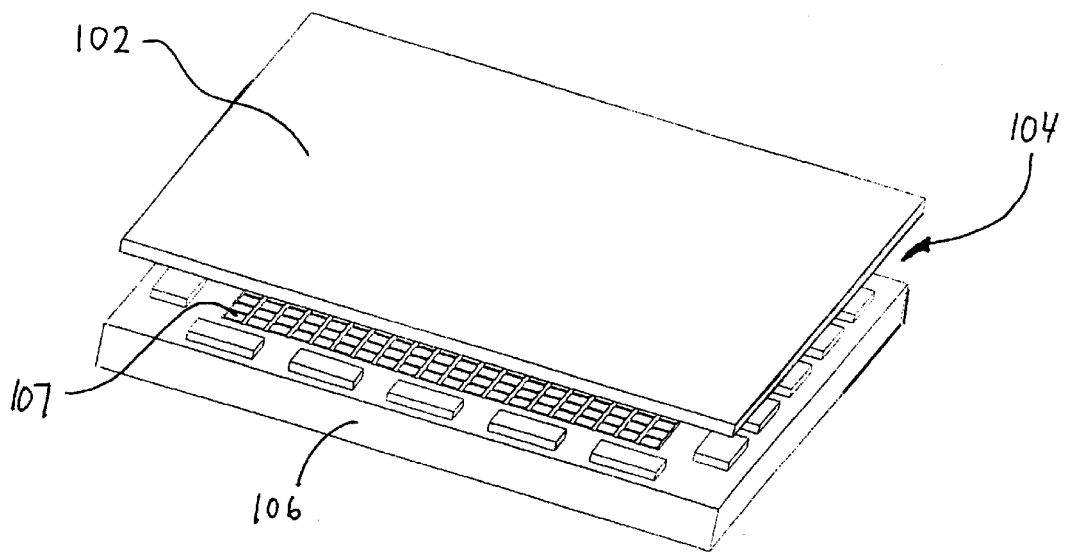
Fig. 1a
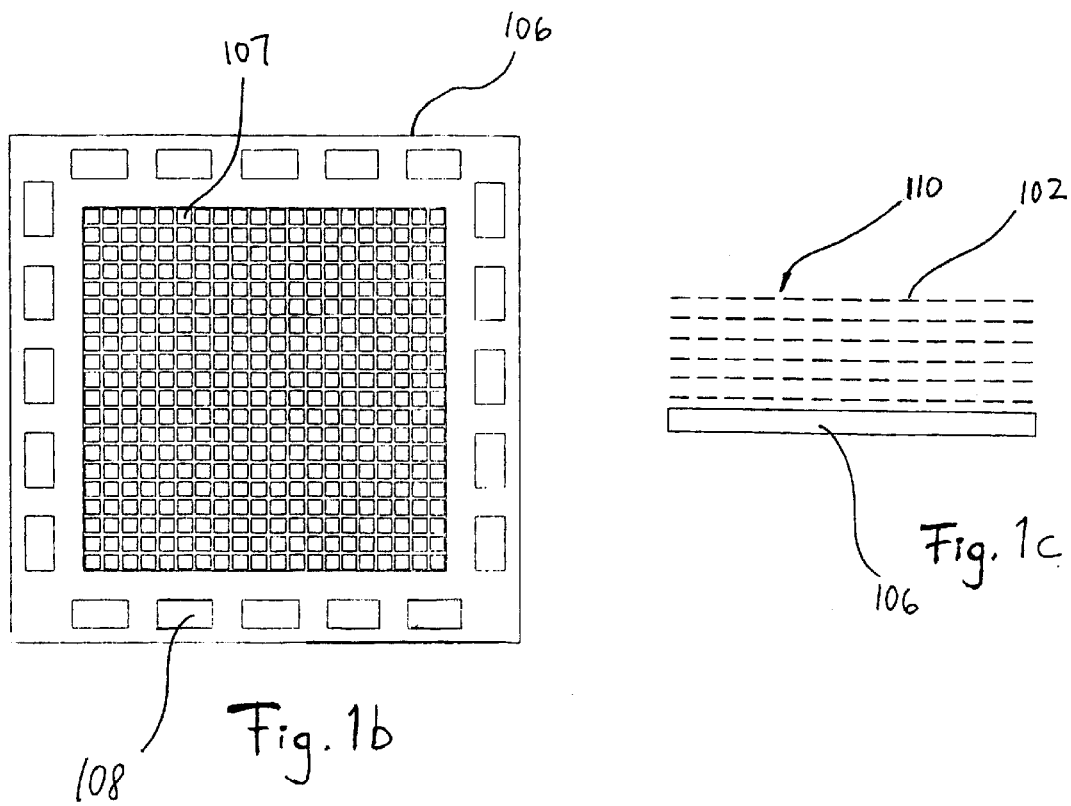
Fig. 1b
Fig. 1c

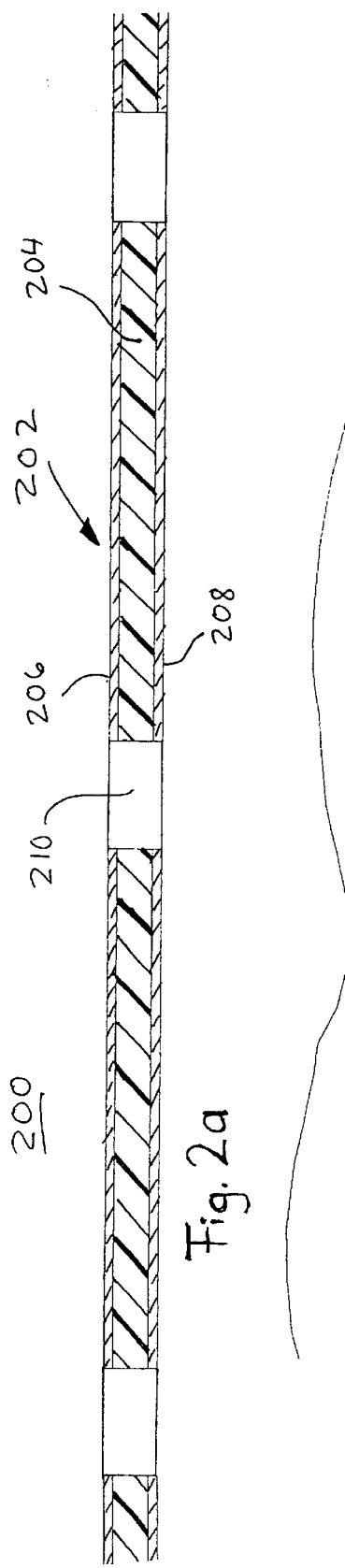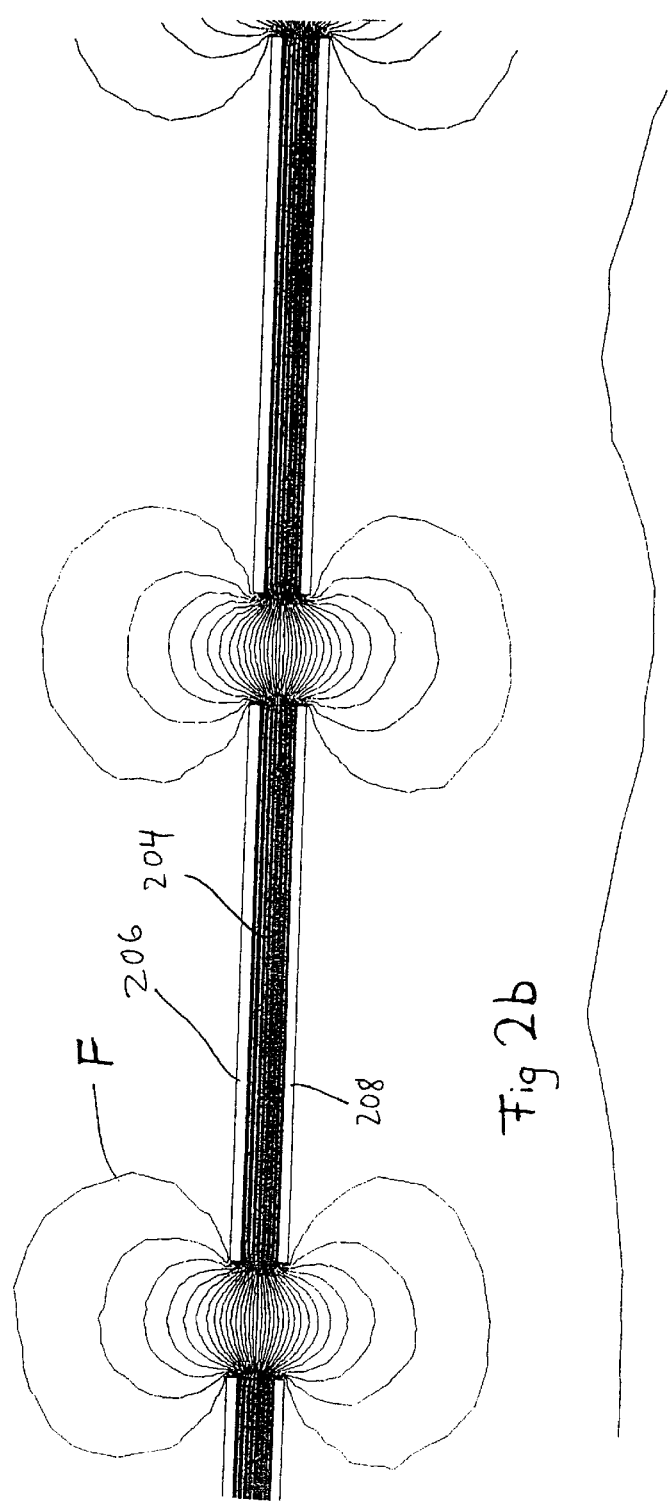

DIAGNOSTIC AND THERAPEUTIC DETECTOR SYSTEM FOR IMAGING WITH LOW AND HIGH ENERGY X-RAY AND ELECTRONS

The present invention relates to a general X-ray and electron imaging device, particularly useful for verification, control and optimization of radiation treatment of cancer as well as for applications like diagnostic X-rays, non-destructive testing and screening of containers and vehicles in airports and in customs. More particularly it relates to a detector system with high efficiency over a wide range of photon and electron energies, from diagnostic X-rays starting from the low energies of a few keV all the way up to a hundred MeV, i.e. energies that are of interest and used in radiation therapy or for imaging of large and/or dense objects.

BACKGROUND OF THE INVENTION

Real time electronic detectors have during the last 30 years revolutionized many areas of X-ray imaging. This includes diagnostic modalities like computed tomography for detailed imaging of the human head and body as well as image intensifiers and video techniques for imaging of the cardiovascular system and for airport security. There are several advantages with real time electronic detectors including improved detection efficiency, wider dynamic range and instantaneous response. Digital images also allow immediate display, electronic storage, diagnosis through telecommunication and computer-aided detection, on-one image enhancement and diagnosis. In spite of the obvious advantages with digital imaging it has turned out to be very hard to replace current film-screen combinations in applications demanding high spatial resolution over large areas, in particular when constraints like high tolerance to radiation damage and reasonable cost are added. Despite its advantages film has a number of disadvantages such as low efficiency, limited dynamic range, noise and the need for chemical development.

The working principle of the present range of electronic detectors is that photons transmitted through the irradiated object are converted to electrons through electromagnetic interactions. Those electrons are in some devices collected directly by dedicated sensors or they are guided through some fluorescent material where secondary light is created and this light is in turn detected by a sensor like e.g. a CCD. In imaging devices for higher X-ray energies, a special converter is added in front of the detector to increase the probability for electromagnetic interaction of the X-rays. This is needed to increase the efficiency of the devices since higher energy X-rays are much more penetrating and would otherwise pass the detector undetected. The converter is usually made as a thin plate of some heavy metal like copper or iron, but molybdenum, chromiun or tungsten are equally suitable. In principle any material could be used, but the efficiency of the device will increase with increasing atomic number. Thus, an atomic number greater than 20 is preferable.

For the purpose of this application the term "electromagnetic interactions" should be taken to encompass all physical interactions between photons and matter that causes generation of at least an electron, i.e. via Compton effect, pair-production or photo electric effect.

The term "conversion" is meant to encompass any process involving a photon, wherein some or all of the energy of that photon is transferred to some other corpuscle and wherein a free electron is produced as a result of said energy transfer. Thus, a "converter" is any device capable of producing this effect. It could simply be a gas enclosed in a volume, wherein incident photons interact with the gas in the photo-electric effect to produce electrons. It can also be a sheet or other type of structure of a solid material, in which electrons are generated via the Compton effect or by pair production (electron—positron generation).

"Amplification" is to be construed as a process where one electron interacts with atoms or molecules of a gas thereby causing ionization thereof to produce a plurality of electrons and "holes" (positive gas ions). Thus, "amplification" is meant to encompass both primary ionization regardless of whether there is an electric field present or not, as well as the well known avalanche fenomenon that occurs in electric fields of the order of $10^4$ V/m or more.

Thus, an "amplifier" will encompass any structure that causes such "amplification" it could e.g. simply be a gas enclosed in a volume where incident electrons will interact with the gas, or a more complex device where an electric field is generated.

Radiation therapy and surgery remain the main modalities for cancer cure in the industrialized world. Radiation therapy is used for more than half of the new cancers with permanent cradication of the tumor without severe complications in more than half of the cases. The radiation dose is delivered to the patient in different fractions, one fraction a day over a period of a couple of weeks. Alignment of the radiation field relative to the tumor is of paramount importance. The alignment has to be particularly accurate when intensity modulation is used and the tumor is close to sensitive organs like the spinal cord. Positioning errors should by no means exceed 2 to 5 mm depending on treatment site. Monitoring and controlling the treatment with a detector behind the patient is usually referred to as portal imaging. More recently, it has been shown that a correction of the patient set-up using the information from an Electronic Portal Imaging Device (EPID) increases the probability of a complication free tumor cure in the order of 10%. However, as already indicated, film still remains the most common tool for verification and quality control of the treatment and is used in more than 90% of the cases. The EPID's has proven valuable since digital images allow electronic storage and processing of the data. They also in principle enable an on-line control and verification of the treatment even if this is difficult because of the low efficiency of the present EPID's and the corresponding relatively long times for data acquisition. They also facilitate an adaptive real time control during the course of delivery of the different fractions of the treatment. In portal imaging, it is obvious that the detectors need to be highly radiation tolerant and this is a severe constraint one has to take into account when designing the detector.

There are two main types of EPID systems available commercially today: One is a mirror-based video system and the second is an electronically scanned liquid-ionization chamber system. In both cases, the incident photons are converted to electrons with an efficiency of about 5%–8% through interactions in a metal plate, typically 1.5 mm of copper. If the metal is made thicker, scattering of the electrons in secondary reactions is becoming a problem and electrons will stop in the metal. The typical range for 1 MeV electrons in Cu is less than 0.7 mm. This range is approximately proportional to the energy of the electrons. This puts a fundamental limit on the obtainable efficiency for these devices. Both approaches have proven valuable in localizing the patient in the radiation field and verification of the radiation therapy. A major drawback is that the contrast and quality of the resulting images only makes the bone structure visible and not internal organs and the tumor itself, the exact position of these organs remains unknown. The only way of being sure about these positions would be diagnostic X-ray images taken with the patient in the actual treatment position, without movement of the patient and right before the actual treatment starts since any movement would cause change in position of the internal organs. Unfortunately existing EPID's are almost insensitive to X-rays of diagnostic energies.

The main specific drawback with the video system is its low efficiency due to loss of photons in the process of de-magnifying the fluorescent screen through a mirror, lens or fiber optic taper to the camera. This efficiency is in fact less than 0.01%. Another problem is the inherent bulkiness of the system that may hamper patient set-up and make them difficult to use in machines with beam stoppers to stop the radiation beam after passing the patient.

In the liquid-ionization chamber the pixels are scanned by a switched high voltage one row at a time and the currents from the pixels are read out by a row of 256 electrometers, the whole detector consist of an array of 256×256 pixels with a spacing of 1.27 mm. This generates a current of typically 50 pA and the noise is around 0.5 pA. The liquid is integrating the created charge for around 0.5 s and it takes around 5 s to get an image. The drop in efficiency due to the scanning is thus a factor 10. Limitations are long-time stability of the ultra-clean liquid and pick-up due to the high-voltage switching.

The most promising emerging EPID seems to be amorphous silicon arrays. They have been developed since around 1990 but are not yet a commercial product. Advantages compared to the video system are much better optical coupling (around 50%) between the fluorescent screen and the detector since the array is positioned in close proximity to the screen and there is no demagnification. Each pixel is controlled by an a-Si transistor, one row of pixels is gated at a time, and the accumulated charge is amplified by a row of preamplifiers and digitized by a 12 bit ADC. Amorphous silicon has the advantage that it can be deposited over large areas but is not ideal for fabrication of transistors; the ON resistance usually exceeds mega-ohms and this slows down the readout of the charge. In spite of enormous investments from the flat-panel display industry it is not trivial to manufacture large arrays without defects and the cost for a large instrumented a-Si array for X-ray imaging (~25×25 $cm^2$ size) is very high. The efficiency is also for this device limited by the fact that only 6%–8% of the incident photons interacts at all in the detector.

The trend in radiation therapy is towards conformal intensity modulated treatments and hyperfractionation that reduces the dose per treatment field. This increases the demands on the EPID in terms of efficiency, high quality image for alignment checks should be obtained at dose levels of 0.01 Gy corresponding to an image acquisition time of 0.25 s at a dose rate of 2 Gy per minute. For a total dose for the field of 1 Gy this means the treatment maybe aborted at radiation levels of less than 1% of the single field dose in case of misalignment. The intended set-up may be documented through either a simulator or a digitally reconstructed radiograph (DRR), which has been reconstructed for a certain beam set-up using computed tomography. Potentially this will enable computer-aided on-line detection of misalignments of the radiation field.

If one compares the EPID to for example an upgrade in accelerator equipment for the treatment unit the cost for an EPID would be less than 0.15 M$ while a new accelerator would cost about 2 M$. Since a portal imager would have very significant impact on estimated benefits for the patient in terms of increased probability of eradicating the tumor, it is in reality a very cost-effective device compared to other investments. If the effect on the outcome of the treatment is 10%, this corresponds to about 1,5 million more patients saved in the U.S. per year.

SUMMARY OF THE INVENTION

Thus, there is still a strong need in this field for a detection means that allows an adaptive real time control during the course of delivery of radiation during treatment. In addition, it would be advantageous if the same detection system could be used for both low and high-energy photons, such that for quality control purposes in medical care, a high quality image could be obtained before therapeutic irradiation begins. Furthermore, it would be advantageous if there need be no physical shift or replacement of the detection unit between high and low energy detection, i.e. the detector units should not need to be moved or damaged due to exposure to high energy radiation.

These objects are achieved with a device, method and system as defined in the appended claims.

In particular the present invention in a preferred embodiment concerns detectors comprising a plurality of amplifier and converter stages.

The spatial resolution is determined by the pixel pitch, which will be around 1 mm in the prototype detector, but could be taylored to suit the application in question. This is not a very competitive resolution for diagnostic medical imaging but is sufficiently high for portal imaging. The portal imager according to the invention will also be used as a detector for diagnostic X-rays. It may not be the optimum detector for this task but it will provide valuable additional high-contrast images to correct for internal displacements of sensitive organs as well as the target with the patient in the actual treatment position. To use separate X-ray detectors for all these tasks is impractical. With some modifications the system can also be used for precision dosimetry and current mapping of therapeutic radiation fields. It can thus be used to optimize the dose delivery with different radiation treatment units and techniques.

A particular advantage with a preferred embodiment of the detection system according to the present invention is that it allows the contrast of images produced to be optimized to a high degree and also makes it possible to determine the elemental composition of different parts of the object. This is achieved by the provision of gain control for each individual amplifier in the stack, whereby detection of photons can be discriminated between high and low energies.

Further advantages with the invention are:

1) Possibility of an order of magnitude higher efficiency compared to present detectors for high energy X-rays due to use of multiple conversion layers in combination with efficient collection of the signals from each conversion layer. The integral signals from all the individual layers are detected by one single matrix of sensors.

2) A high signal to noise ratio due to the amplification of the signal in the gas.

3) High radiation resistant since no active electronics need to be directly exposed to the beam, if desired.

4) Very fast parallel read-out enabling acquisition of the whole image matrix in less than 3 ms, if desired.

5) The energy response of the detector can be changed simply by altering the potential on the different electrodes.

6) Rugged design where the amplification is geometrically stable but adjustable.

7) Highly efficient over a wide range of energies. This enables the combination of an detector for diagnostic and therapeutic X-rays in one single device by using a thin entrance window and gas volume on top of the first converter layer. If a diagnostic X-ray tube is inserted above the patient a high contrast diagnostic X-ray image could be obtained right before the treatment starts and thus the exact position of any organs and the tumor itself could be determined.

8) Energy sensitive if desired. This makes it possible to optimize the contrast for any given imaging task and also opens the possibility to determine the elemental composition of the object. This energy sensitivity also enables dual-energy imaging in the sense that it is possible to determine not only the X-ray attenuation in the object but also the different elements the object consist of by comparing images with different weighting of low and high energy X-rays.

9) The invention also offers the possibility to weight the information from X-rays of different energies in such a way that the contrast in the resulting image is optimized for the object of interest.

BRIEF DESCRIPTION OF THE DRAWINGS

FIG. 1a is a perpective view of a basic embodiment of a detecor according to the invention;

FIG. 1b is a schematic top view of a charge collector according to the invention;

FIG. 1c is a schematic side view of a stack of converters on top of a charge collector;

FIG. 2a is a schematic view of a GEM structure suitable for use with the invention;

FIG. 2b shows equipotential lines for a biased structure as shown in FIG. 2a;

FIG. 7b shows schematically equipotential lines for biased structure of FIG. 7a;

DETAILED DESCRIPTION OF PREFERRED EMBODIMENTS

The basic principle behind the invention will now be described with reference to FIGS. 1a and b showing the most general embodiment of a detector according to the invention.

Figure 5:
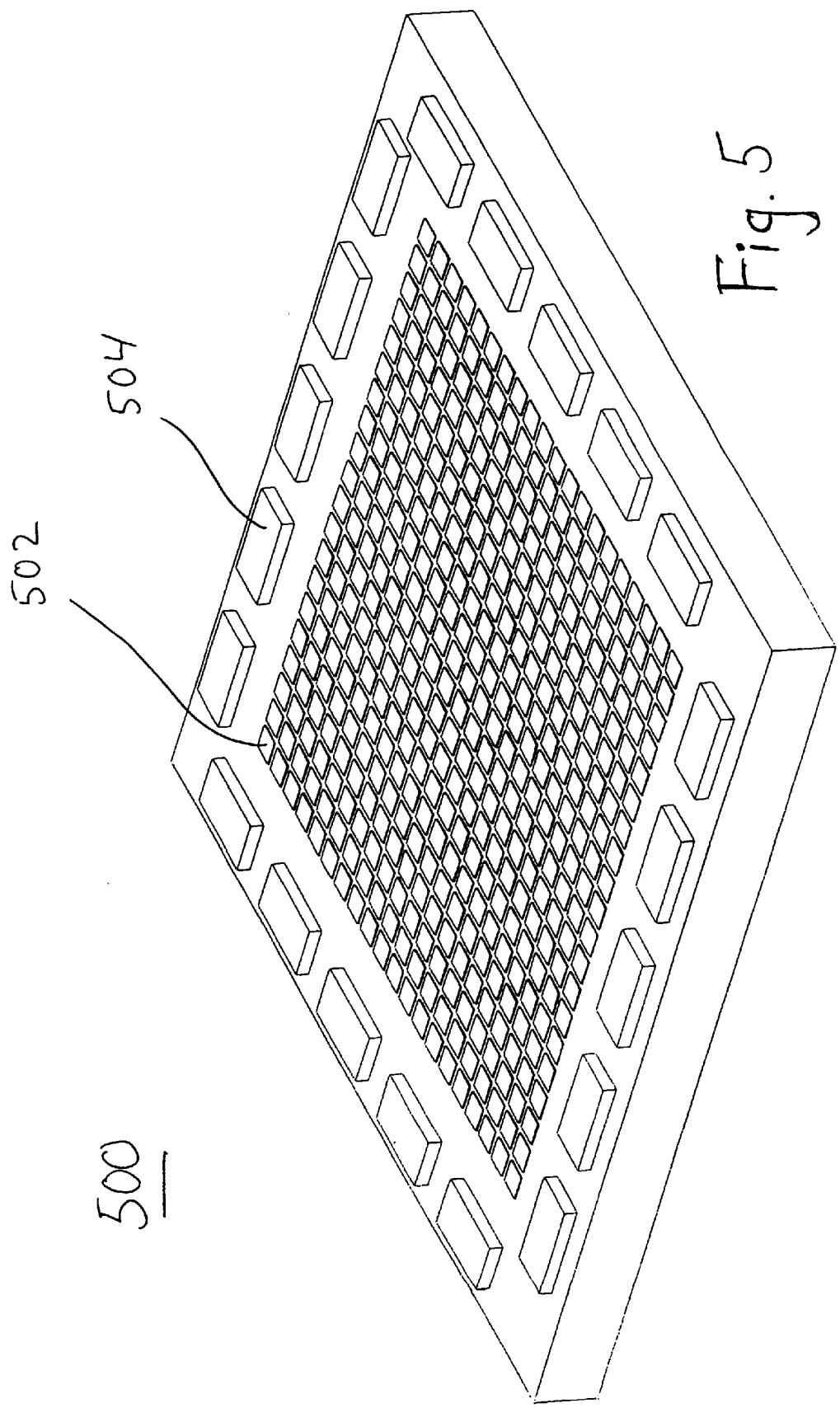
FIG. 5 is a perspective view of a charge collector according to the invention.

This figure shows an X-ray to e converter 100 in the form of a sheet 102 of a heavy metal, e.g. Cu, about 1.5 mm thick. Below this converter there is an air gap 104 of about 1 mm, and at the bottom there is a multi-layer PCB 106 (Printed Circuit Board) (described more in detail with reference to FIG. 5 below). Briefly it comprises pads 107b, 1 mm$^2$, distributed over the surface of a polymer board, and connected to ASIC inputs 108 positioned at the edges of the PCB (see FIG. 1b).

X-rays on the converter sheet 102 will generate electrons in the metal, exiting into the air gap 104. The negatively charged electrons will ionize the gas, and the electron signal will be amplified through an avalanche in the gas if the field in the gap 104 is 10$^4$ V/m or higher. The secondary electrons will be collected on the electrode pads at ground potential. If there is a gas volume above the converter sheet 102 and the top cover (not shown) is made essentially transparent to diagnostic X-ray energies, the device can be used as a detector for diagnostic purposes too. This requires that the converter 102 be perforated such that the electrons can be drifted through the holes 110. In addition to If several converters are stacked the efficiency will be increased. This is shown schematically in FIG. 1c. By applying an appropriate voltage across the stack and by selecting the thickness and hole diameter appropriately for the converter sheets, it is possible to obtain avalanche amplification in the holes 110 in the perforated converter sheets 102.

Another way of achieving amplification is to provide a separate amplifier device. Several such devices are known, and one type is designated Gas Electron Multipliers (GEM).

Referring now to FIG. 2a there is shown the main component of such a GEM, generally designated 200. It is a thin composite mesh 202 acting as proportional avalanche amplifier in gas counters (U.S. patent pending, Sauli et al).

The mesh consists of a thin insulating foil 204, e.g. of Kapton®, which is metal-clad 206, 208 on both sides, a suitable metal being Cu, and perforated by a regular matrix of holes 210. The holes may be 100 $\mu$m wide. The insulating foil 204 may be 50 $\mu$m thick, the thickness of the metal cladding 206, 208 being 5 $\mu$m. This structure is located in a confinement containing a gas. This gas, when exposed to ionizing radiation of some kind, will dissociate into electrons with negative charge and corresponding ions with positive charge. If a potential difference (typically 500 V) is applied across the insulator/between the two metal clad sides of the composite mesh 202 structure, a dipole field F will develop in the holes 210, sec FIG. 2b (the lines shown are equipotential lines, and thus the filed lines are perpendicular to these lines). Electrons released by the ionization in the gas will drift towards the high field through the holes/channels 210, and will be focussed therein. The focussed electrons will then be amplified through avalanche multiplication of the electrons in the high electric field region. The amplified signal of electrons could be detected by e.g. a Multi-Wire Proportional Chamber (MWPC), a Micro Strip Gas Chamber (MSGC) or a Printed Circuit Board (PCB). With a device like this amplification factors above 10000 have been reached. It is also known to combine two GEM's by arranging them in a cascade at some distance, or in electrical contact.

Devices of this kind were originally developed for the detection of ionizing radiation in high-energy physics experiments. However, as indicated previously, these known devices are also suitable for detecting X-rays of diagnostic energies up to around 100 keV through conversions in the gas. At higher energies, the probability for the X-rays to interact in the gas will decrease and the efficiency will drop towards zero.

Figure 3:
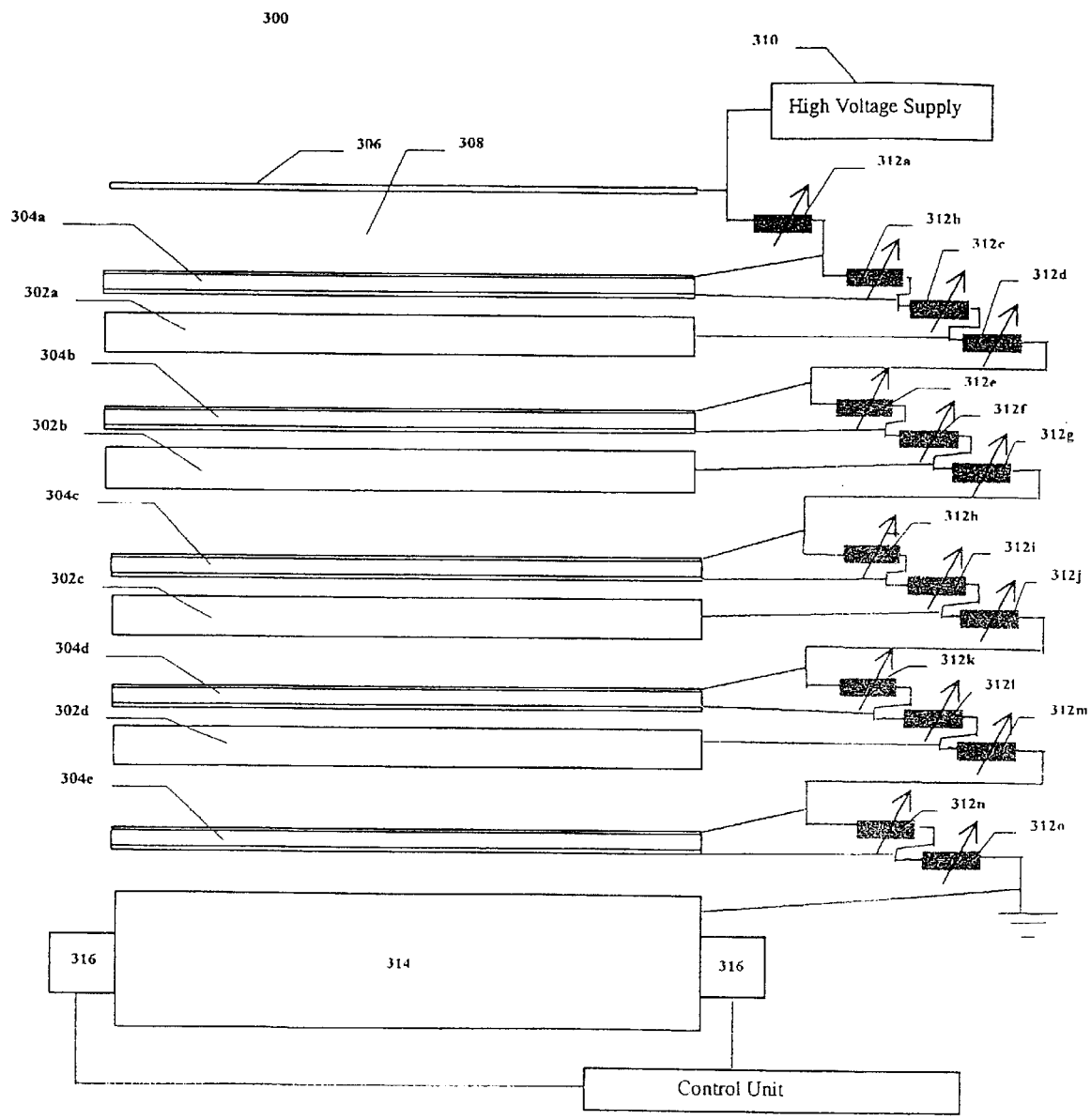
FIG. 3 is a schematic overview of a preferred embodiment of a detector unit according to the invention.

Turning now to FIG. 3 there is shown schematically a preferred embodiment of the detector according to the invention generally designated 300.

It comprises a stack of alternating converters 302 and amplifiers 304. The entire stack is located inside a housing (not shown) containing a suitable gas, e.g. Xe, although there is a large spectrum of possible gases to choose from like other noble gases such as e.g. Ar, Ne. Also mixtures of gases are conceivable, in particular it is a standard technique to mix in a so called quencher that will make the avalanches more controllable and make the detector less prone to sparks and discharges. Examples would be $CO_2$ or dimethylalcohol (DME). The gas or gas mixture may or may not be pressurized, or it could be provided at sub-atmospheric pressure. The higher the gas pressure, the more ionizations in the gas will take place per unit path length of a charged particle such as e.g. an electron.

The top cover 306 of the housing is preferably thin and light to maximize the number of low energy diagnostic X-rays reaching the gas volume at the top, i.e. as many of the X-ray photons as possible should be transmitted therethrough. A suitable material would be thin metal foil, e.g. Al, or the like. Other possible materials are polymers of various kinds, e.g. MYLAR®. Generally speaking materials with low atomic numbers are suitable. An at present preferred embodiment of the device according to the invention comprises as an amplifier device the above mentioned GEM (Gas Electron Multiplier) (for simplicity the perforations of converters and amplifiers have been left out). At present it is believed that the use of GEM's is the best mode of operating the invention.

The other component, the converter 302, comprises a sheet of material having the ability to convert the incident photons into electrons through electromagnetic interactions. Preferably, a material with high cross-section for this reaction will be used. The converters have been positioned below each said GEM type structure. However the uppermost layer is an amplifier, for amplifing signals generated in the top gas volume 308, just below the top cover 306. In this volume low energy photons (diagnostic X-rays) will react and generate electrons.

The converter sheet 302 made of heavy metal is perforated (not shown in this figure), which are aligned with the holes (not shown) in said GEM structure. The converter sheet is preferably 0.1 mm to 1 mm thick depending on the field of application of the invention. The sheets may also be progressively thicker towards the bottom of the stack compared to the sheets in the top in order to match the higher occurrence of lower energy X-rays in the top layers relative to the bottom layers These sheets are referred to as converter layers since the photons impinging in such a sheet will create charged particles (electrons and positrons) and the forward momentum of the photons will be transferred to the electrons, such that electrons will exit from the sheet into the gas volume 308 beneath the top cover 306. There the electrons will cause ionization of the gas and give rise to the order of 10 electron-ion pairs on average. Those electrons will be collected and multiplied in the first amplification stage 304a. As indicated above, the amplifier in the structure may consist of said GEM type structure. The metal layers of the GEM's are biased with a voltage of typically 500 V etch. However, the voltage is variable in certain ranges such as from negative voltage (if you want to block the signal from above) up to 1000 V. By controlling the voltage certain beneficial effects are obtainable, which will be described below.

Each amplifier layer can be individually biased at a desired voltage/potential difference across the insulator with a suitable voltage source 310. This could most easily be provided by arranging a series of variable resistors 312, such that the voltage across each amplifier layer 304 simply is adjusted by adjusting the series resistance associated with that particular layer. Thus, each amplifier stage is coupled in a way such that it can be set at the desired potential by a common external voltage source. In the shown embodiment there is a resistor chain 312a, 312b . . . 312o, coupled in series across the entire stack. The means for controlling the voltage across each amplifier is not critical and any other means that achieves the same result is useable within the scope of the invention. For example, each layer could of course be connected to an individual voltage source. In the shown example the external voltage across the entire stack is about 6000 V, and the voltage across each amplifier layer may be adjusted to between 0 and 1000 V.

For the top amplifier layer 304a it is contemplated that the voltage bias for special purposes may be set to be reversed, i.e. in some cases the potential difference is set such that electrons scattered from the patient or other object and containing no relevant information, will not contribute to the signal.

GEM's would be only one possibility to achieve the desired charge collection and amplification that is needed in combination with the converter layers.

Figure 4:
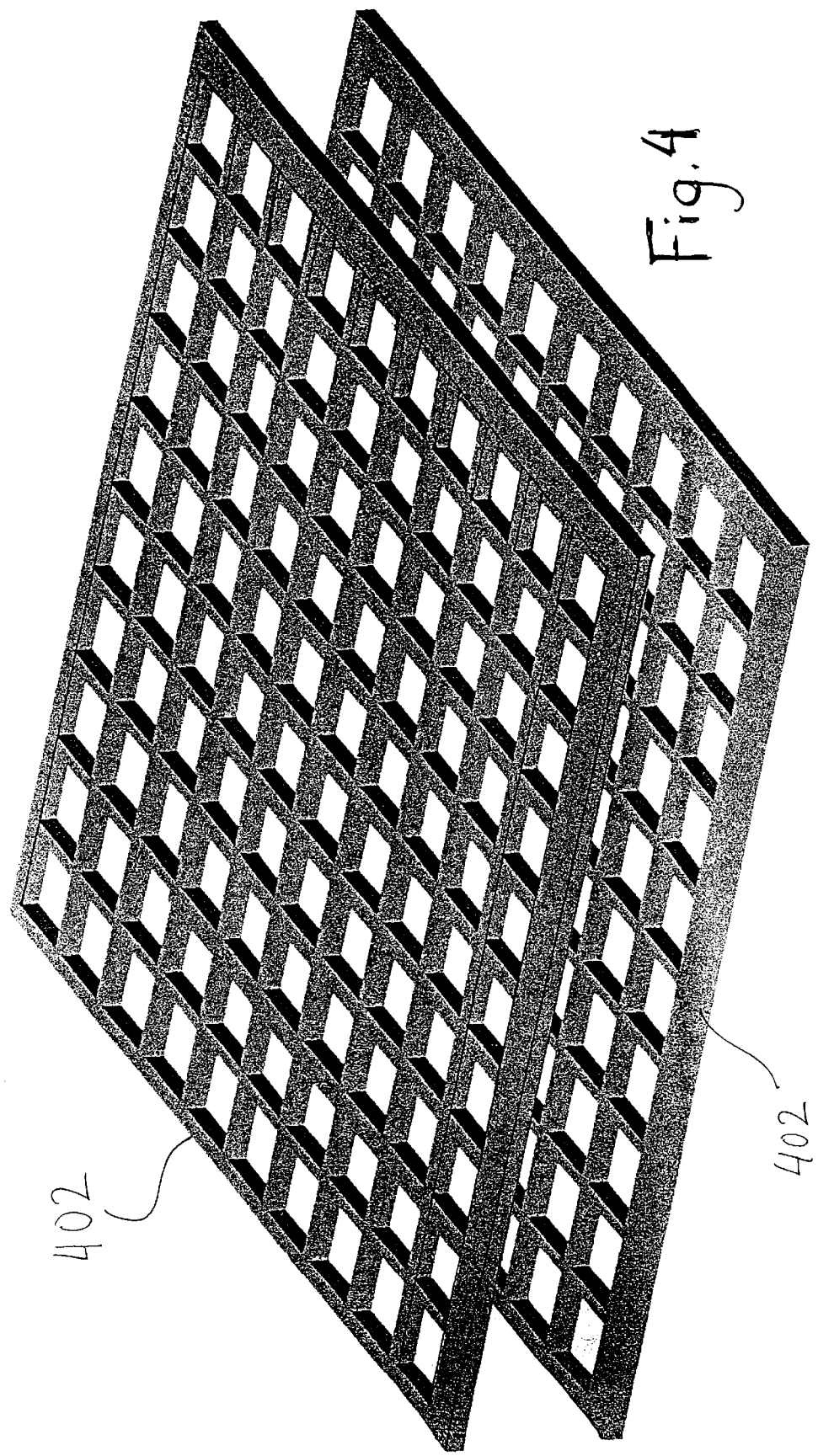
FIG. 4 is a perspective view of an embodiment of the detector comprising a mesh structure.

Another means of obtaining the desired charge collection and amplification would be to combine the converter layers (perforated with holes) with wire meshes 402 (see FIG. 4). The potential difference between the wire mesh 402 and the converter should be high enough to start avalanche multiplication.

This double layer structure of "converter and amplifier" can be repeated a number of times, where a practical number could be 5–8, but could also be higher, or lower, for specific applications.

At the bottom of the stack of converter and amplifier layers there is a Printed Circuit Board (PCB) 314 for collecting charge and which is coupled to read-out electronics 316 that provide data to a control unit 318, e.g. a computer. The signals can be routed to the edge of the board through state of the art multi-layer PCB's (see FIG. 5 which is a schematic illustration of a charge collector according to the invention comprising a PCB), and the electronics sensitive to the radiation (such as diodes, transistors or other semiconductor devices) can thus, in accordance with the invention, be positioned at the edge outside the radiation field and can even be shielded to be protected against scattered radiation. As indicated such PCB's per se are state of the art and in FIG. 5 a PCB based charge collector 500 is shown in a perspective view.

It may comprise 20 layers of an insulator such as FR4. Between each layer there are metal conductors provided, each of which are connected to one charge collection pad 502 each through holes, metal plated on the inner circumference, said conductors extending towards the edges of the board. The pads are preferably made of Cu, Au or Al, although other metals are conceivable, and are about 0.8 mm wide and about 5 $\mu$m thick. They are made using conventional photolithografic techniques well known in the art. The pads are distributed so as to correspond to the geometry of the holes in the converter and amplifier matrices, i.e a center to center distance of about 1 mm.

The most important feature of the PCB is that there is a large number of pads 502 distributed over the board. Each pad must have its own connection to an input of e.g. an ASIC 504. If, as preferred, the ASIC's are mounted at the edges of the board, the PCB is made in a layered structure, wherein the leads connecting the pads with the electronics are drawn in respective layers. The optimum design of such a PCB is made by so called auto-routing, a standard technique well known to the skilled man in the field of printed circuit board design. Suitable software for auto-routing can be obtained from Cadence, under the trade name SPECTRA.

Other types of charge collecting means are conceivable in less radiation intense environments, e.g. an ordinary CCD. Most likely different tools to achieve the charge collection and avalanche amplification will be used for different applications, the essential idea according to the invention being the mixing of layers of converters with layers for amplification and charge collection means to achieve an efficient detector for high energy X-rays.

Instead of collecting the electrons with pads on a printed circuit board and measure the charge for each pads as the signal proportional to the number of x-ray photons (or fluence) in one pixel there are other possibilities to read out the signal for each pixel. One way is to convert the electrons to visible photons at the bottom of the detector and have the bottom transparent to those photons.

In an ordinary avalanche in the gas there is at least as many photons produced as electrons and thus the photons may be produced in an amplifier at the bottom of the detector. Another way of producing the photons is to have the electrons incident on a fluorescent screen at the bottom of the detector where the electrons will induce emission of photons in this screen The photons created in any of these ways will in turn be detected by a sensor sensitive to photons such as for example a CCD. The photons may be guided to the CCD sensor through suitable optics such as mirrors and lenses.

Figure 6:
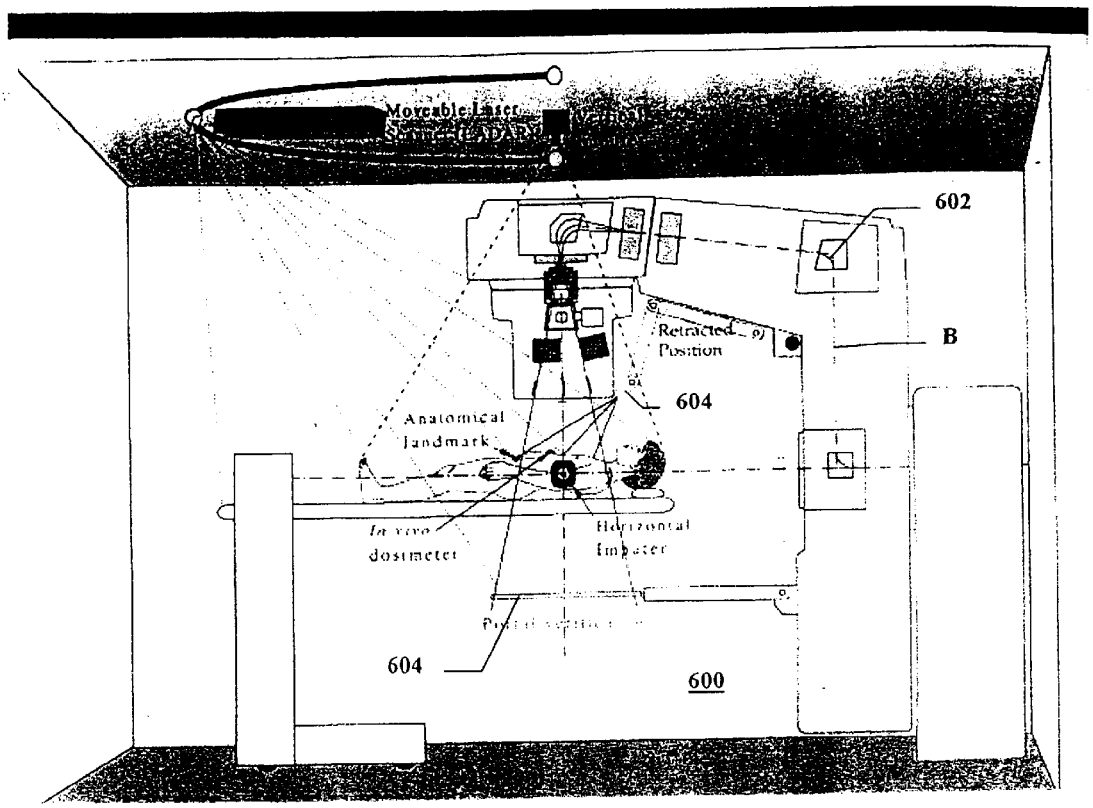
FIG. 6 schematically shows a set-up for radiation therapy.

In FIG. 6, there is shown a schematic of a set-up 600 for radiation therapy with external X-ray photons or electrons. An accelerator (not shown) is situated in a neighboring room, and a beam of electrons B is directed through collimators towards the patient's body. If X-ray photons are desirable, a suitable target 602 is placed in the electron beam at appropriate location. If electrons are desired of course, no target is used. The beam (X-rays or electrons) is swept with a modulated intensity. A portal imager 604 according to the invention may be positioned either directly below the patient or below the treatment coach, as indicated in the figure. Also, there is provided a complementary diagnostic X-ray tube 606, which is positioned above the patient. When the patient is exposed to diagnostic X-rays, the portal imaging device will function as a detector for diagnostic X-rays in the 50 keV range.

The function of a portal imaging device according to the embodiment shown in FIG. 3 will now be described with reference to the set-up of FIG. 6 and to FIG. 3. We assume operation with photons, i.e. X-rays. Thus, for the production of therapeutic radiation, a linear accelerator is provided. It produces electrons in the energy range 1–50 MeV. These electrons are directed via suitable optics into the space where a patient to be treated is placed. A target (e.g. Be) is positioned such that the electrons impinging thereon produces X-ray photons, which are collimated and directed to the area on the patient's body where therapy and/or diagnosis is to be performed.

For diagnostic purposes, a standard X-ray tube positioned above the patient is used. The energy of such photons is around 50 keV. The photons exiting beneath the patient will impinge on the gas volume 308 at the top of the detector unit, comprising the stack of amplifiers 304 and converters 302. A significant fraction of the diagnostic X-rays will interact in this gas volume 308, mainly through the photo-electric effect. The ionization in form of electrons created by the photoelectron will be collected and amplified by the uppermost amplification structure 304a. Almost all diagnostic X-rays remaining after passing the gas volume 308 will be stopped in the first converter 302 (intended for high energy X-rays) and will create a negligible amount of detectable ionization. This first diagnostic image can be used for aligning the patient appropriately, e.g. if there should any risk of sensitive tissues being exposed to the highly energetic therapeutic X-rays that are to follow.

In the following moment the radiation therapy beam will be turned on, if there is no need to correct the position of the patient based on the information from the diagnostic X-ray image. The gas volume 308 will be more or less transparent to those high-energy X-rays. Since the gas volume 308 may still get hit by scattered electrons from the patient that does not contain much image information, it may be preferable to e.g. put the drift field to zero in the gas volume 308 to get rid of this background noise. The majority of these electrons will stop in the first converter layer 302a. The high-energy photons will penetrate into the stack and the photons with lower energy will predominantly convert in the top layers 302a, b, c while the photons with relatively higher energy will dominate in the bottom layers 302n, n-1, n-2. Secondary Compton photons will also penetrate down the stack and depending on the angle through which they are deflected, this will smear the position resolution as you go down in the stack. Since the contrast is higher for low energy photons the information content will presumably be higher in the top layers. By tuning the voltage determining the amplification for each layer it is possible to weight the contribution from the different layers to obtain a maximum contrast. It is also possible by way of comparing two images where higher and lower energy photons are weighted differently to roughly estimate the energy of the incident X-rays. From this estimate it is possible to deduce an elemental composition of the object. This may in particular be of value for non-medical applications, e.g. When looking for explosives in screening for air port security.

The attenuation of the x-rays in the object will mainly depend on the density (rho) and the atomic number (Z) of the object. Those two quantities are usually not possible to distinguish from each other, but since the dependence for each quantity is different as a function of x-ray energy this is actually possible with a detector that gives an estimate of the energy of the incident x-rays. As an example one could imagine first obtaining an image with the photons converting in the first half of the stack of converters/amplifiers weighted much higher comparing to photons converting in the second half. This will be an image predominantly made up of lower energy photons. Secondly one could register an image with the photons converting in the second half of the stack of converters/amplifiers. This will be an image consisting predominantly of higher energy photons. The number of x-ray photons detected in the two images will depend on the elemental composition of the object. This difference can be measured for different test objects of known composition. It is thus possible to calibrate the expected response for different materials. One can also compare the measurements to computer simulations of the spectrum and record images with one multiple weightings of the x-ray spectrum and compare the results to get a more detailed estimate of the elemental composition.

Figure 7A:
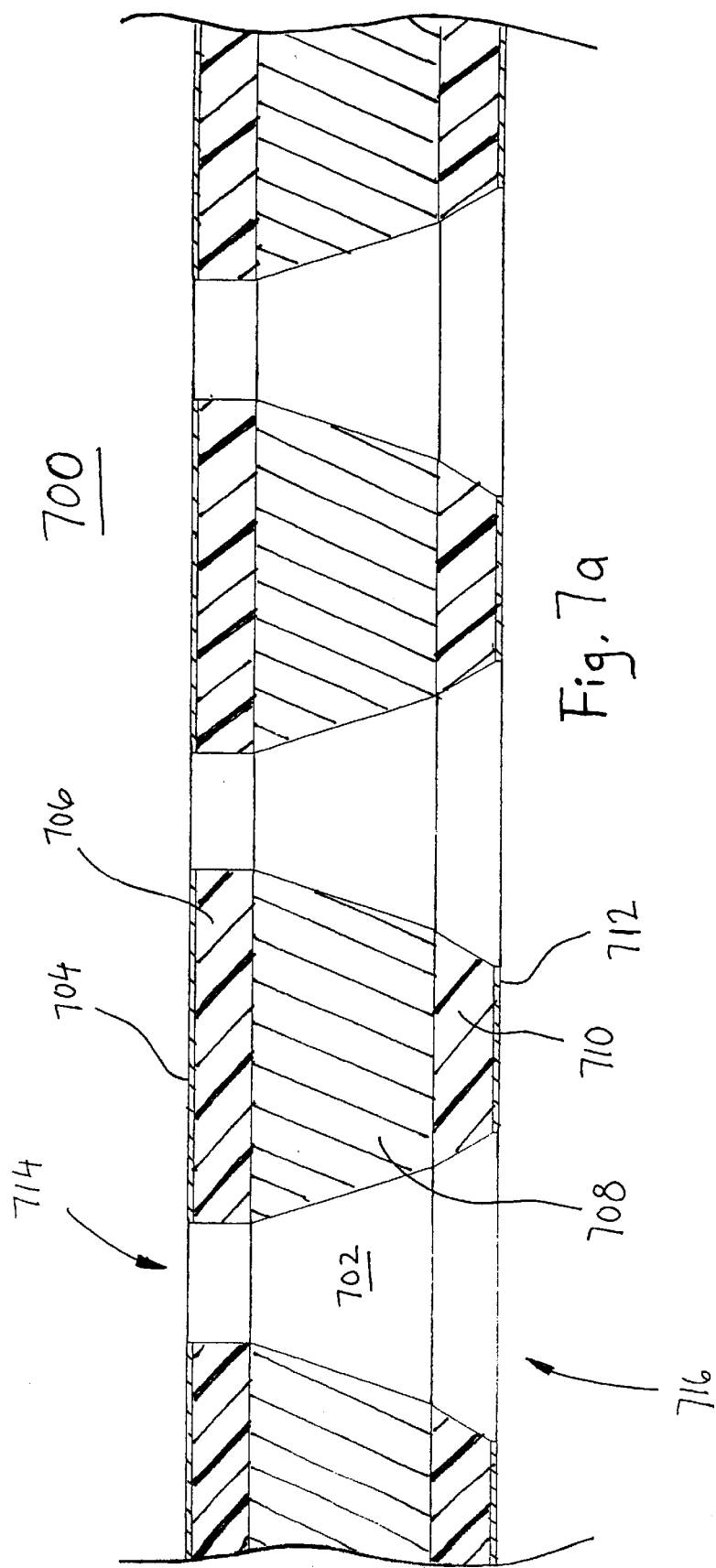
FIG. 7a illustrates an alternative structure for a further embodiment of the detector according to the invention.
Figure 7B:
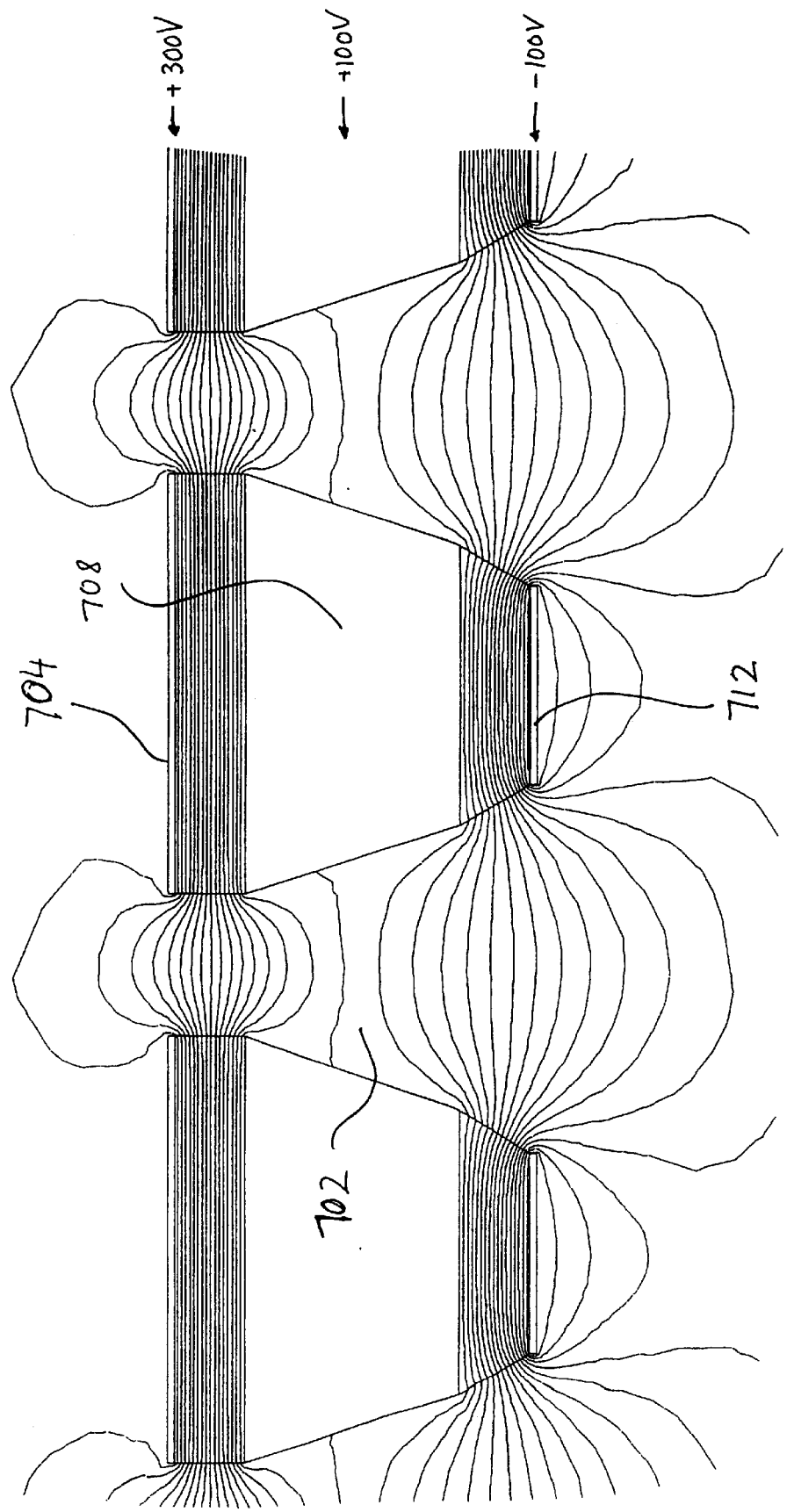

In FIGS. 7a–b a preferred embodiment of an amplifier/converter structure according to the present invention is disclosed, generally designated 700.

FIG. 7a is a cross section of one perforated sheet 700, forming a composite layered dipole structure, comprising holes 702 through which electrons may move. The sheet is comprised of a first (or top) metal layer 704, about 5 µm thick. This metal layer 704 has been deposited on an insulating material forming a first insulating layer 706, similar to the known GEM structure described above with reference to FIG. 2. Underneath the insulating layer 706 there is a thick metal layer 708, which is at least one order of magnitude thicker than the top metal layer, in the shown embodiment it is 150 µm thick. Below the thick metal layer 708 there is a second insulating layer 710, on which there is deposited a second (bottom) metal layer 712. The layers 710 and 712 preferably have the same compositions and thicknesses as the layers 704 and 706. The entire sheet is made by suitable known depostion methods.

When the composite sheet has been made, the holes 702 are made by etching. Being an unisotropic process, the etching will have the effect of creating "funnel" like holes, as is clearly shown in FIG. 7a. Thus, the "entrance" opening 714 for electons has a smaller diameter that the "exit" opening 716. The actual slopes of the inner walls of the holes 702 is not necessarily as shown in the figure, but will vary depending on the materials selected for the layers and on the particular etching process employed. The known GEM structure shown in FIG. 2, having a much thinner overall thickness does not exhibit such outspoken funnel-like holes. This particular structure with such "funnel"-like holes 702 has certain benefits for the purpose of the invention, which will be described below.

The structure of FIG. 7a will function as a composite amplifier/converter. Thus, as shown schematically in FIG. 7b, which is an image obtained by simulation, a voltage is applied across the entire structure such that the first (top) metal layer 704 is at approximately +300 V, the thick converter layer 708 is at approximately 100 V, and the second (bottom) metal layer 712 is at −100 V. Of course these values can vary within relatively wide limits depending on where in the stack the actual structure is situated, and what one wants to achieve in the structure in question. The lines are equipotential lines, and thus the field has a direction perpendicular to the potential curves. As can be seen in FIG. 7b there will be an electric field inside the holes 702, the density of which is highest in the upper part of the holes 702, i.e. in the region of the first insulating layer 706. By virtue of the holes "flaring" out downfield, electrons passing through the holes 702 will have less probability of diffusing into the thick metal layer 708, and thereby the efficiency of the structure becomes higher. The bottom part of the structure comprising insulating layer 710 and bottom metal layer 712, does not function as an amplifier in the sense of the corresponding structure of layers 704 and 706. Rather the function is to provide enhanced guiding of the electrons out from the holes 702 and to further prevent the potential diffusion of electrons into the converter metal layer 708. Of course by suitable selection of voltage applied also the lower part of the structure could be used for amplification purposes.

Figure 9:
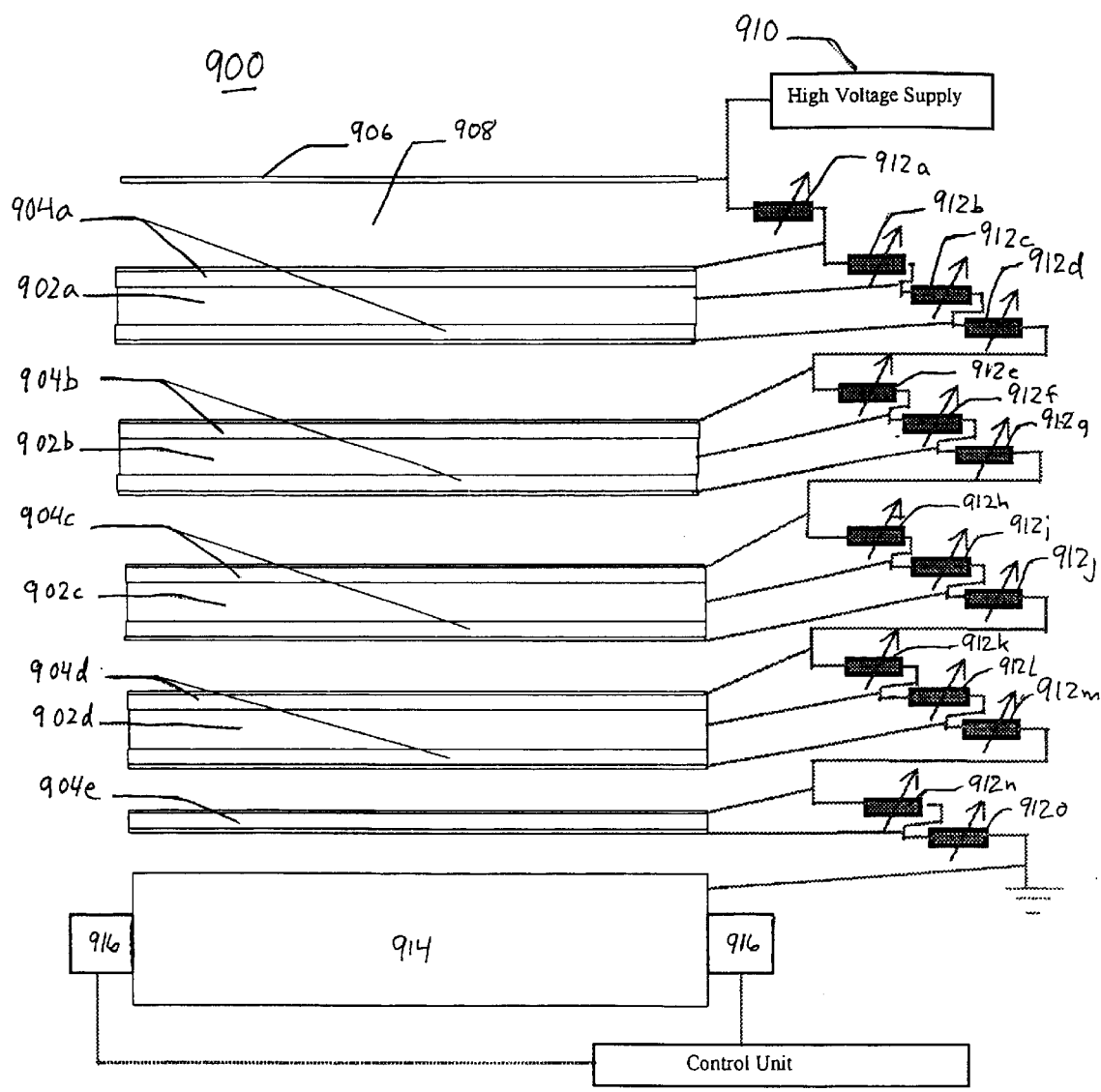
FIG. 9 is a schematic overview of still another preferred embodiment of a detector unit according to the invention.

These composite dipole layered structures 700 may be arranged in the same way as shown in FIG. 3, just substituting the alternating converters 302n and amplifiers 304n for such a composite structure 700. A set-up for use of the embodiment of the structure shown in FIG. 7 is disclosed in FIG. 9 and generally designated 900.

Thus, a plurality of composite layered structures 902a–d, 904a–d is stacked above each other enclosed in a housing (not shown). A top cover 906 is provided and a gas volume 908 is formed between the top cover and the first composite structure 902a, 904a. At the bottom of the stack there is provided a PCB 914 having read-out electrinocs 916 connected thereto, which in turn are coupled to a control unit.

The composite structures can be individually biased at a desired voltage/potential difference across the insulator with a suitable voltage source 910, similar to the embodiment in FIG. 3. This could most easily be provided by arranging a series of variable resistors 912a–o, such that the voltage across each amplifier 904 in the composite structure simply is adjusted by adjusting the series resistance associated with that particular layer. Thus, each amplifier stage is coupled in a way such that it can be set at the desired potential by a common external voltage source. In the shown embodiment there is a resistor chain 912a, 912b . . . 912o, coupled in series across the entire stack. The means for controlling the voltage across each amplifier is not critical and any other means that achieves the same result is usable within the scope of the invention. For example, each layer could of course be connected to an individual voltage source. In the shown example the external voltage across the entire stack is about 6000 V, and the voltage across each amplifier layer may be adjusted to between 0 and 1000 V.

Figure 8:
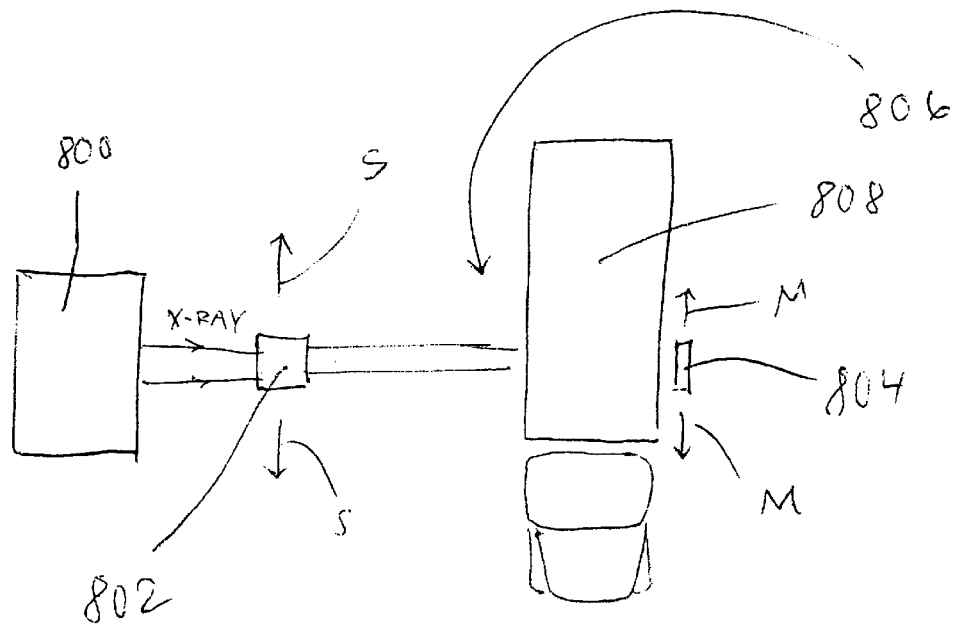
FIG. 8 illustrates schematically a set-up for cargo screening.

In FIG. 8 an application of the invention for cargo screening is shown schematically in a top view. The set-up comprises a source of X-rays 800, in the energy range up to 50 MeV, e.g. a linear accelerator. Collimators 802 are provided for collimating the X-rays. There is provided an arrangement for scanning/sweeping the beam over a relatively large area, indicated schematically by arrows S. Furthermore there is provided a detector 804 according to the invention, arranged such there will be a space 806 between the radiation source 800, 802 and the detector 804, large enough for a large object, such as a lorry 808 to be positioned therebetween. Because the detector can be made only in a limited size, there is provided means for moving the detector in an X-Y plane such that when the radiation beam has scanned one area corresponding to the size of the detector, it can be moved so as to cover a previously unscanned area (the movement of the detector is indicated by arrows M). In operation of the system a large cargo carrying object, such as a container, truck, trailer etc, will be positioned in the space 806 between an X-ray source and a detector according to the invention. The radiation will be turned on and the interior of the object can be checked for its content, in relatively short time. As an alternative to move the detector, the entire object could be moved. A truck or other vehicle could e.g. be moved by its own engine.

The invention having thus been described, it should be understood that various modifications can be made without departing from the inventive concept, which is defined by the appended claims.

For example, the detector can be used to study dose distributions. This can be done in air or in a so called water phantom, which is a simulation of body tissue. For such applications the material in the detectors are selected to mimic body tissue, i.e. polymers having carbon and nitrogen contents similar to that of living tissue.

Also, it is conceivable to use the device for imaging during electron therapy. In such a case of course the converter would not be operable since the therapeutic electrons themselves are detected.

It is also to be understood that the detector may be optimized by a skilled man for other types of particles, such as neutrons, protons, atomic nuclei of various kinds etc.

What is claimed is:

1. A detector unit for detecting photons in the energy range 1 keV to 100 MeV, comprising:
    at least two non-gas converter layers stacked on one another and for interacting with incident X-ray photons and causing electrons to be emitted therefrom;
    at least one amplifier coupled to each converter and adapted to interact with the electrons emitted from the converter to produce a multiplicity of secondary electrons and photons representing a signal proportional to the incident fluence of X-ray photons;
    connectors connecting the detector to an electric field generating means for providing an electric drift field for secondary electrons in the detector; and
    a sensor device arranged to receive said signal and provide an input to electronic signal processing means.

2. The detector as claimed in claim 1, comprising a housing enclosing said converter(s) and amplifier(s), and a gas provided inside said housing.

3. The detector as claimed in claim 2, wherein the housing comprises a top cover essentially transparent to low energy X-ray photons.

4. The detector as claimed in claim 2, wherein
    a first of said at least two stacked converter layers is adapted to interact with and record incident X-ray photons of a first energy range, and
    a second of said at least two stacked converter layers is adapted to interact with and record incident X-ray photons of a second energy range,
    wherein each of the first and second stacked converter layers is adapted to selectively record a different energy range.

5. The detector as claimed in claim 1, wherein said converter comprises a sheet of a material with an average atomic number sufficiently large that a fraction greater than 1% of incident X-rays are converted.

6. The detector as claimed in claim 1, wherein said converter comprises a sheet of a heavy metal selected from the group consisting of Cu, Fe, Mo, Cr and W.

7. The detector as claimed in claim 1, wherein said amplifier comprises a composite dipole layered structure, said composite structure being perforated with holes.

8. The detector as claimed in claim 7 wherein said composite dipole structure comprises a sheet of an insulating material which is metal clad on both sides.

9. The detector as claimed in claim 8 wherein said converter comprises a perforated sheet and wherein each perforation has a dimension such that it covers at least one each of said holes in said amplifier.

10. The detector as claimed in claim 7, further comprising connectors connecting each amplifier to a voltage source for applying a voltage across each layer to create an electric field over the dipole structure, the density of which is higher within said holes, thereby to cause a drift of electrons through said holes.

11. The detector as claimed in claim 1, wherein said converter and said amplifier are integrated in one unit by the provision of a composite dipole layered structure comprising a sheet of an insulating material which is metal clad on both sides, wherein at least one of said metal claddings is substantially thicker than the sheet of insulating material, said thicker metal cladding acting as a converter.

12. The detector as claimed in claim 11 wherein said thicker metal cladding is provided on the bottom side of said insulating sheet, and wherein the upper metal cladding is sufficiently thin to achieve an electric field for providing efficient charge collection.

13. The detector as claimed in claim 11 comprising a central metal layer on both sides of which there is provided an insulating layer, and wherein the respective insulating layers each are provided with a metal film, wherein the central metal layer is thicker than each insulating layer, and wherein each insulating layer is thicker than each metal film.

14. The detector as claimed in claim 13 wherein said composite dipole layered structure is perforated with holes.

15. The detector as claimed in claim 14, wherein said holes have an entrance opening for electrons and an exit opening wherein said exit opening is wider than said entrance opening.

16. The detector as claimed in claim 1, having a composite dipole layered structure, comprising a sheet of an insulating material which is metal clad on both sides, wherein said insulating material acts as a converter.

17. The detector as claimed in claim 1, wherein said connection means comprise a resistor chain coupled in series across the entire detector unit including converters and amplifiers such that the voltage across each amplifier and converter is selectable and variable.

18. The detector as claimed in claim 1, wherein said converter and said amplifier are integrated into one composite layered structure, such that at least one of said layers in said amplifier constitutes said converter.

19. The detector as claimed in claim 1, wherein said sensor device is a charge collection device arranged to collect said secondary electrons.

20. The detector as claimed in claim 1, wherein said sensor device is an optical sensor device arranged to detect said photons.

21. A system for X-ray therapy and diagnosis, comprising:
    at least one source of X-rays;
    collimators for said X-rays for providing a defined amount of radiation to a patient; and
    a detector as claimed in claim 1.

22. A detector unit for detecting photons in the energy range 1 keV to 100 MeV, comprising:
    at least two converter layers stacked on one another and adapted to interact with incident X-ray photons and to cause electrons to be emitted therefrom;
    at least one amplifier coupled to each converter and adapted to interact with the electrons emitted from the converter to produce a multiplicity of secondary electrons and photons representing a signal proportional to the incident fluence of X-ray photons;
    connectors connecting the detector to an electric field generating means for providing an electric drift field for secondary electrons in the detector; and
    a sensor device arranged to receive said signal and provide an input to electronic signal processing means,
    wherein said amplifier comprises a wire metal mesh, and wherein there is provided connecting means for connecting a voltage source to apply an electric potential between the converter and said wire mesh.

23. A detector unit for detecting photons in the energy range 1 keV to 100 MeV, comprising
- a housing having walls, a top cover and a bottom and enclosing a gas;
- a plurality of integrated converter and amplifier structures arranged in a stack in said housing;
- a charge collection device arranged at the bottom of the housing;
- connection means comprising a variable resistor chain coupled in series across the entire detector, connectable to an external voltage source;
- electronic read out devices coupled to said charge collection device for providing an input to a control unit; wherein
- said integrated converter and amplifier structures each comprise a central metal layer on both sides of which there is provided an insulating layer, and wherein the respective insulating layers each are provide with a metal film forming a composite dipole layered structure, wherein the central metal layer is thicker than each insulating layer, and wherein each insulating layer is thicker than each metal film, and wherein said composite dipole layered structure is perforated with holes; said holes having an entrance opening for electrons and an exit opening wherein said exit opening is wider than said entrance opening.

* * * * *